United States Patent [19]

Hayashi et al.

[11] Patent Number: 4,749,701
[45] Date of Patent: Jun. 7, 1988

[54] AMINOSTYRYL COMPOUND, LEUKOTRIENE ANTAGONISTIC COMPOSITION CONTAINING THE SAME AS EFFECTIVE INGREDIENTS AND METHOD OF ANTAGONIZING SRS BY EMPLOYING THE SAME

[75] Inventors: Yoshio Hayashi; Tomei Oguri, both of Ushiku; Masaki Shinoda; Kazuo Takahashi, both of Ibaraki, all of Japan

[73] Assignee: Mitsubishi Chemical Industries Limited, Tokyo, Japan

[21] Appl. No.: 941,807

[22] Filed: Dec. 15, 1986

[51] Int. Cl.[4] .................. A61K 31/505; C07D 239/26; C07D 239/30; C07D 239/34
[52] U.S. Cl. ..................... 514/247; 544/224; 544/235; 544/283; 544/336; 544/349; 544/358; 544/402; 544/403; 546/112; 546/164; 546/175; 546/201; 546/229; 546/238; 546/246; 546/247; 548/326; 548/371; 548/378; 548/469; 548/482; 548/511; 548/560; 548/565; 514/248; 514/249; 514/255; 514/256; 514/258; 514/259; 514/311; 514/315; 514/415; 562/433; 562/442; 560/37
[58] Field of Search ............... 546/112, 164, 175, 201, 546/229, 238, 246, 247; 562/433, 442; 260/501.11; 514/311, 247, 248, 249, 255, 256, 258, 259, 315, 415; 544/224, 235, 283, 336, 349, 358, 402, 403; 548/326, 371, 378, 469, 482, 511, 560, 565; 560/37

[56] References Cited

U.S. PATENT DOCUMENTS

| | | | |
|---|---|---|---|
| 2,095,457 | 10/1937 | Steindorff et al. | 562/433 |
| 2,427,286 | 9/1947 | Knapp et al. | 514/311 |
| 2,508,860 | 5/1950 | Grimmel et al. | 562/433 |
| 3,018,290 | 1/1962 | Sauers et al. | 562/433 |
| 3,152,042 | 10/1964 | Wood et al. | 514/311 |
| 3,574,704 | 4/1971 | Claassen et al. | 562/433 |
| 3,947,493 | 3/1976 | Balme et al. | 562/433 |
| 3,957,850 | 5/1976 | Bouchara | 562/433 |
| 4,101,671 | 7/1978 | Keck et al. | 546/112 |
| 4,296,129 | 10/1981 | Kadin | 260/501.11 |
| 4,681,884 | 7/1987 | Grozinger et al. | 544/224 |

*Primary Examiner*—Richard L. Raymond
*Assistant Examiner*—Raymond Covington
*Attorney, Agent, or Firm*—Oblon, Fisher, Spivak, McClelland & Maier

[57] ABSTRACT

Disclosed are an aminostyryl compound represented by Formula I:

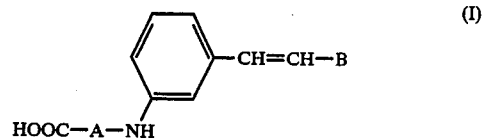

wherein A represents a linking group having 3 to 4 chain members; B represents an unsubstituted or substituted 5 to 6-membered monocyclic type heterocyclic residue containing 1 to 2 hetero atoms, an unsubstituted or substituted condensed heterocyclic residue which contains 5 to 6-membered monocyclic type heterocycle containing 1 to 2 hetero atoms, a naphthyl group or an alkyl group having 5 to 7 carbon atoms, a composition having leukotriene antagonism which contains an aminostyryl compound represented by Formula I as the effective ingredient, and a method of antagonizing SRS based on leukotriene antagonistic activity by employing the same.

8 Claims, No Drawings

AMINOSTYRYL COMPOUND, LEUKOTRIENE ANTAGONISTIC COMPOSITION CONTAINING THE SAME AS EFFECTIVE INGREDIENTS AND METHOD OF ANTAGONIZING SRS BY EMPLOYING THE SAME

BACKGROUND OF THE INVENTION

This invention relates to a novel aminostyryl compound having leukotriene antagonistic action and a leukotriene antagonistic composition containing the same as the active ingredient.

For prophylaxis or therapy of allergic diseases, there are the method which inhibits liberation of the mediator of anaphylaxis and the method which permits an antagonist to act on the mediator liberated. Disodium cromoglycate [The Merck Index, ninth edition 2585 (1976)] and Tranirast [Journal of Japanese Pharmacology, 74, 699 (1978)] are typical drugs belonging to the former and those belonging to the latter may include drugs antagonistic to hystamine which is one of the mediators of allergic reactions such as diphenhydramine, chlorophenylamine, astemizole, terfenadine, clemastine, etc., as well known drugs. However, a substance which cannot be antagonized with an anti-hystamine agent, namely SRS (Slow Reacting Substance) has been suggested to be liberated from the lung of a bronchial asthma patient [Progr. Allergy, 6, 539 (1962)], and recently these SRS [leukotriene $C_4(LTC_4)$, leukotriene $D_4(LTD_4)$ and leukotriene $E_4(LTE_4)$] are comprehensively called SRS [Proc. Natl. Acad. Sci. U.S.A., 76, 4275 (1979) and 77, 2014 (1980); Nature, 285, 104 (1980)] and considered as the important factor participating in human asthma attack [Proc. Natl. Acad. Sci. U.S.A., 80, 1712 (1983)].

Some leukotriene antagonists have been known in patents or literatures. For example, there have been known FPL-55712 [Agents and Actions, 9, 133 (1979)] represented by the following formula:

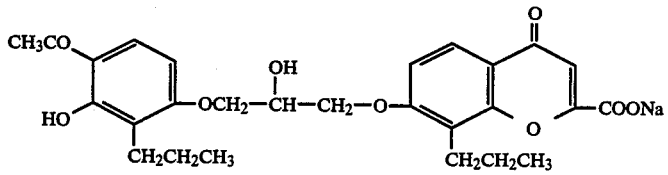

KC-404 [Jap. J. Pharm., 33, 267 (1983)] represented by the following formula:

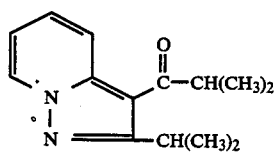

KZ-111 [Chem. Abst, registration number 72637-30-0] represented by the following formula:

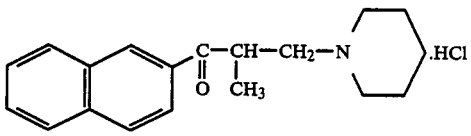

and the compound represented by the following formula (U.S. Pat. No. 4,296,129): represented by the following formula:

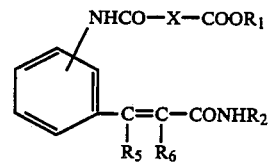

wherein $R_1$ represents a hydrogen atom, an alkyl group having 1 to 4 carbon atoms or a group represented by the following formula:

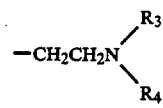

(wherein $R_3$ and $R_4$ each represent an alkyl group having 1 to 3 carbon atoms); $R_2$ represents an alkyl group having 8 to 15 carbon atoms or a cycloalkyl group having 6 to 12 carbon atoms; $R_5$ and $R_6$ each represent a hydrogen atom or a methyl group.

However, none of these have been clinically applied.

As aminostyryl compounds, there have been known compounds (West Germany Pat. No. 23 31 444) represented by the following formulas:

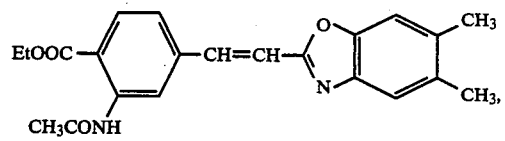

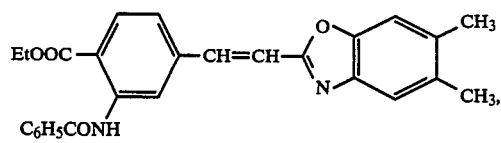

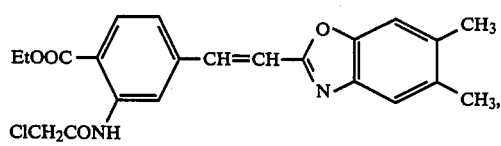

-continued

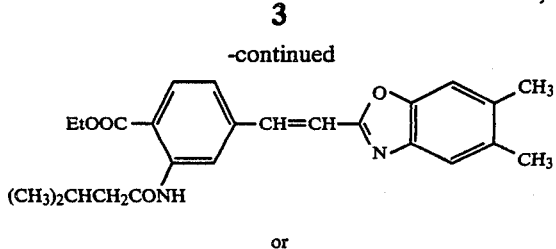

or

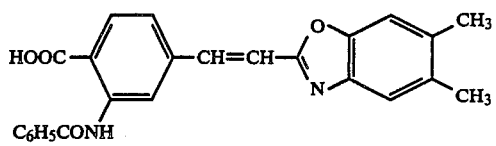

and a compound [Arzneim Forsch, 19, 719 (1969)] represented by the following formula:

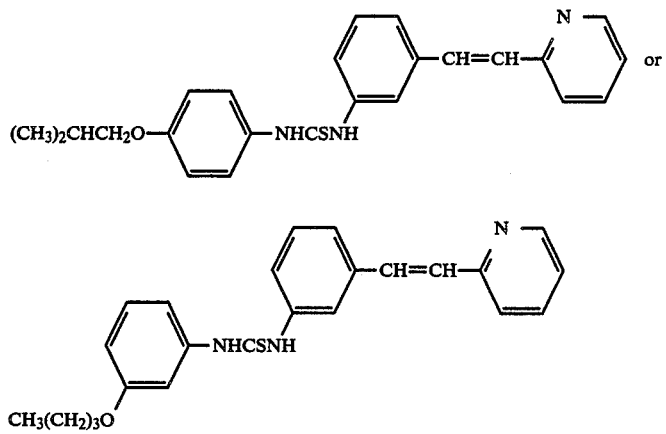

However, in any of these literatures or patents, nothing is mentioned about the leukotriene antagonistic action.

Further, a compound represented by the following formulas:

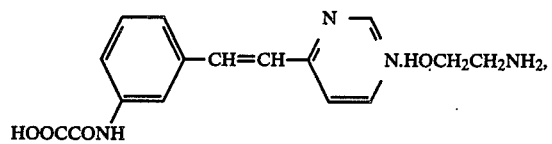

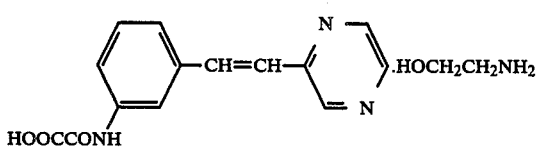

or

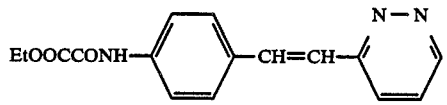

was disclosed in Japanese Unexamined Patent Publication No. 142968/1980, as a novel compound having the antiallergic action and the anti-inflammatory action. However, there is no description about the leukotriene antagonistic action.

SUMMARY OF THE INVENTION

The present inventors have sought after compounds having antagonistic action to leukotriene and effective as the therapeutical medicine for various diseases caused by leukotriene, and consequently found that a novel aminostyryl derivative has excellent leukotriene antagonistic action to accomplish the present invention.

The aminostyryl compound of the present invention is a compound represented by the following Formula I:

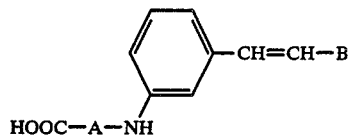

wherein A represents a linking group having 3 to 4 chain members; B represents an unsubstituted or substituted 5 to 6-membered monocyclic type heterocyclic residue containing 1 to 2 hetero atoms, an unsubstituted or substituted condensed heterocyclic residue which contains 5 to 6-membered monocyclic type heterocyclic containing 1 to 2 hetero atoms, a naphthyl group or an alkyl group having 5 to 7 carbon atoms.

DETAILED DESCRIPTION OF THE PREFERRED EMBODIMENTS

In Formula I described above, as the linking group in the definition of A any group having 3 to 4 atoms as the chain members constituting the linking group may be used, however, it should particularly preferably contain carbon atom. Such a linking group may include, for example, $-CH=CHCO-$, $-(CH_2)_mCO-$ (wherein m represents an integer of 2 to 3), $-(CH_2)_n-$ (wherein n represents an integer of 3 to 4),

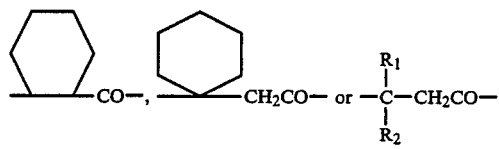

(wherein $R_1$ and $R_2$ each independently represent a hydrogen atom or an alkyl group having 1 to 4 carbon atoms).

The alkyl group having 1 to 4 carbon atoms may include methyl, ethyl, propyl, isopropyl, butyl, isobutyl, sec-butyl, t-butyl group, etc.

As the monocyclic type heterocyclic residue in the definition of B, any residue having 5 to 6-members and containing 1 to 2 hetero atoms may be used. Such a monocyclic type heterocyclic residue may include a 5-membered residue such as furyl, thienyl, pyrrolyl, pyrrolinyl, pyrrolidinyl, oxazolyl, isooxazolyl, thiazolyl, isothiazolyl, imidazolyl, imidazolinyl, imidazolidinyl, pyrazolyl, pyrazolinyl, pyrazolidinyl group, etc.; and a 6-membered residue such as pyridyl, pyrimidinyl, pyrazinyl, pyranyl, piperidyl, pyridazinyl, piperazinyl, morpholinyl group, etc.

As the condensed heterocyclic residue, any residue containing the above described monocyclic type heterocycle may be used, but a residue in which the above described monocyclic type heterocycle and a benzene ring are condensed is particularly preferable. These monocyclic type heterocyclic residue and condensed heterocyclic residue may be substituted with a suitable group, for example, a lower alkyl group such as methyl, ethyl, etc.; a lower alkoxy group such as methoxy, ethoxy, etc.; an amino group, a halogen atom or an aryl group such as phenyl, etc., or an oxo group. The alkyl group having 5 to 7 carbon atoms may include amyl, isoamyl, sec-amyl, sec-isoamyl(1,2-dimethylpropyl), t-amyl(1,1-dimethylpropyl), hexyl, isohexyl(4-methylpentyl), sec-hexyl(1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, heptyl, isoheptyl(5-methyl hexyl), 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, etc.

The aminostyryl compound of the present invention is not limited to a specific isomer, but includes all of geometric isomers, stereoisomers, optical isomers and their mixtures such as racemic modification.

The aminostyryl compound of the present invention can be synthesized according to various methods.

For example, it can be synthesized according to the synthetic routes [A] and [B] shown below.

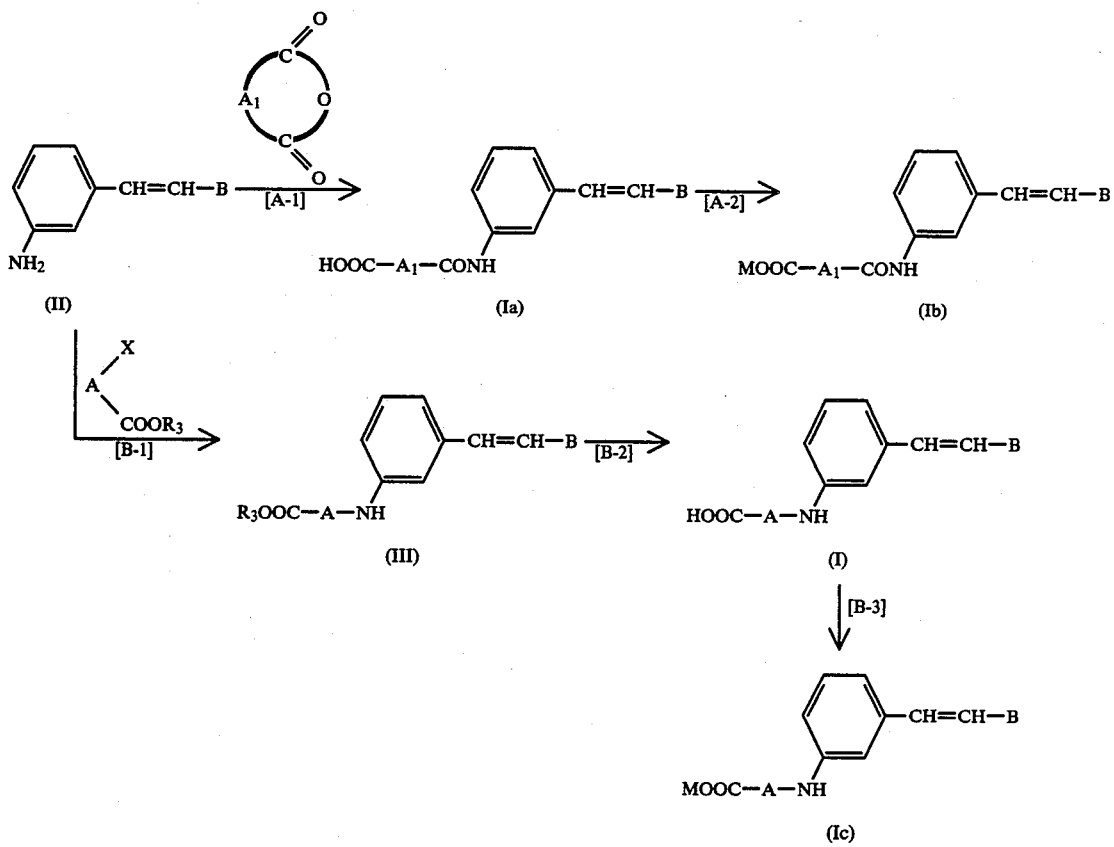

In the synthetic routes, A and B have the same meanings as defined above, $A_1$ represents a linking group having 2 to 3 chain members, M represents an alkali metal atom, X represents a halogen atom and $R_3$ represents an alkyl group having 1 to 5 carbon atoms.

The aniline derivative (II) used as the starting material can be synthesized according to a known method [Tetrahedron Letters, 25, 839 (1984)].

In the synthetic route [A], the aniline derivative (II) is allowed to react with 0.8 to 2 equivalent amounts of a cyclic acid anhydride to obtain the compound (Ia) (step [A-1]). As the reaction solvent, there may be employed aromatic hydrocarbons such as toluene, benzene, etc.; ether type solvent such as ethyl ether, dioxane, tetrahydrofuran, etc.; halogenated hydrocarbons such as chloroform, dichloromethane, etc. This reaction may be carried out at a temperature from under ice-cooling to the boiling point of the solvent, particularly preferably from room temperature to 60° C. The compound (Ia) can be converted to an alkali metal salt (Ib) by the reaction with a carbonate, a hydrogencarbonate or a hydroxide of the corresponding alkali metal in a hydrous alcoholic solvent (step [A-2]).

In the synthetic route [B], a ω-halocarboxylic acid ester can be N-alkylated by the reaction with the compound (II) in the presence of an organic base such as triethylamine, pyridine, etc., in a solvent such as aromatic hydrocarbons, ethers or halogenated hydrocarbons, at a temperature from 0° C. to the boiling point of the solvent to synthesize the compound (III) (step [B-1]). After the compound is hydrolyzed in a conventional manner in a hydrous alcoholic solvent with an alkali metal type inorganic base such as sodium hydroxide, potassium carbonate, etc., the product can be treated with a mineral acid to obtain a free carboxylic acid (I) (step [B-2]). The compound (Ic) can be synthesized according to the same method as in the step [A-2] (step [B-3]).

The compound (I) of the present invention is characterized by having a marked leukotriene antagonistic action.

More specifically, when the antagonistic action to SRS was tested in vitro by use of an extirpated ileum of a guinea pig for the compound of the present invention, it has been found to have a selective antagonistic action for SRS even at an extremely low concentration.

The leukotriene antagonist of the present invention contains the compound represented by the above formula (I) or its pharmaceutically acceptable salt as the active ingredient together with a solid or liquid carrier or diluent for medicine, namely additives such as excipients, stabilizers, etc. When attention is given to the acidity of the carboxylic group of the present compound (I), preferable salts are non-toxic salts which are pharmaceutically acceptable such as alkali metal salts and alkaline earth metal salts such as sodium salts, pottasium salts, magnesium salts, calcium salts or aluminum salts. It is similarly preferable to use adequate non-toxic amine salts such as ammonium salts, lower-alkylamine [e.g. triethylamine] salts, hydroxy lower-alkylamine [e.g. 2-hydroxyethylamine, bis-(2-hydroxyethyl)amine, tris(hydroxymethyl)aminomethane or N-methyl-D-glucamine] salts cycloalkylamine [e.g. dicyclohexylamine] salts, benzylamine [e.g. N,N'-dibenzylethylenediamine] salts and dibenzylamine salts. When the compound (I) of the present invention has a basic rediue or a substituent, preferable salts may include non-toxic salts such as hydrochlorides, methanesulfonates, hydrobromides, sulfates, phosphates, fumarates, succinates, etc. These salts are water-soluble and hence most preferable when used for injections. In said leukotriene antagonist, the proportion of the active ingredient to the carrier component in therapy may be variable between 1 wt.% to 90 wt.%. The leukotriene antagonist may be administered orally in the dosage form such as granules, fine particles, powders, tablets, hard capsules, soft capsules, syrup, emulsion, suspension or solution, or alternatively administered intravenously, intramascularly or subcutaneously as injections. Also, it can be used as topical administration preparation to rectum, nose, eye, lung in the dosage form such as suppository, collunarium, eye drops or inhalent. Further, it can be used in the form of powder for injection which is to be formulated when used. It is possible to use an organic or inorganic, solid or liquid carrier or diluent for medicine suitable for oral, rectal, parenteral or local administration, for preparation of the leukotriene antagonist of the present invention. Examples of the excipient to be used in preparation of a solid preparation may include lactose, sucrose, starch, talc, cellulose, dextrin, kaolin, calcium carbonate, etc. Liquid preparations for oral administration, namely, emulsion, syrup, suspension, solution, etc., contain inert diluents generally employed such as water or vegetable inert diluents oils, etc. These preparations can contain, in addition to the inert diluent, auxiliary agents such as humectants, suspension aids, sweeteners, aromatics, colorants or preservatives. It may also be formulated into a liquid preparation which is contained in capsules of absorbable substances such as gelatin. As the solvent or suspending agent to be used for production of preparations for parentheral administration, namely injections, suppositories, collunarium, eye drops, inhalent, etc., there may be employed, for example, water, propylene glycol, polyethylene glycol, benzyl alcohol, ethyl oleate, lecithin, etc. As the base to be used for suppository, there may be included, for example, cacao fat, emulsified cacao fat, laurine fat, Witepp sol, etc. The preparations can be prepared according to conventional methods.

The clinical dose, when used by oral administration, may be generally 0.01 to 1000 mg/day as the compound of the present invention for human adult, preferably 0.01 to 100 mg, but it is more preferable to increase or decrease suitably the dose depending on the age, condition of disease and symptoms. The above mentioned dose per day of the leukotriene antagonist may be administered once per day or in 2 or 3 divided doses per day at suitable intervals, or intermittently.

On the other hand, when used as an injection, it is preferable to administer continuously or intermittently 0.001 to 100 mg/administration as the compound of the present invention to human adult.

According to the present invention, a novel aminostyryl compound having remarkable leukotriene antagonistic action can be provided. Said aminostyryl compound is useful as the leukotriene antagonist for prophylaxis and therapy of various diseases in which leukotriene participates.

The present invention is described in more detail by referring to Synthesis examples, Examples and Test examples, but these are not intended to limit the scope of the present invention at all. In Synthesis examples and Examples, the symbols of "IR" represents "infrared-absorption spectrum", "IR" being measured according to the KBr tablet method unless otherwise specifically noted.

SYNTHESIS EXAMPLE 1

Synthesis of 2-(trans-3-nitrostyryl)quinoline

To 3.1 g of acetic anhydride, 7.2 g of quinaldine and 7.6 g of m-nitrobenzaldehyde were added and the resulting mixture was stirred under nitrogen atmosphere at 160° C. for 4 hours. After completion of the reaction, water was added to the reaction mixture and the resulting solid was collected by filtration and dried. Recrystallization from toluene gave 12.1 g (yield: 88%) of the captioned compound as an yellow powder.

m.p.: 149°–151° C.

IR: $\nu = 1580, 1510, 1335, 955$.

SYNTHESIS EXAMPLE 2

Synthesis of 2-(trans-3-aminostyryl)quinoline

An amount of 20.0 g of 2-(trans-3-nitrostyryl) quinoline was dissolved in 1000 ml of ethanol and 100 ml of conc. hydrochloric acid solution containing 49.0 g of stannous chloride.2 hydride was added thereto at room temperature, and the resulting mixture was refluxed for 5 hours. After the reaction mixture was cooled to room temperature, a 30% aqueous sodium hydroxide solution was added to regulate pH value to 13 and then the precipitated solid was collected by filtration and washed with water. After drying under reduced pressure, the precipitate was recrystallized from toluene to give 15.0 g (yield 84%) of the captioned compound as a pale yellowish white substance.

m.p.: 160°–162° C.
IR: $\nu$=3420, 1585, 1305, 960.

EXAMPLE 1

Synthesis of 2-[trans-3-(3-carboxypropanamide)styryl]quinoline (compound No. 1)

To 20 ml of dimethoxyethane were added 246 mg of 2-(trans-3-aminostyryl)quinoline, 150 mg of succinic anhydride and 164 mg of sodium acetate and the mixture was heated for 2 hours under reflux. After completion of the reaction, the solvent was distilled off and to the residue was added water to heat in water-bath for 15 minutes. The precipitates deposited were collected by filtration and washed with ethyl acetate, followed by drying under reduced pressure to give 318 mg (yield: 92%) of the yellowish white captioned compound.

m.p.: 191°–193° C. (decomposition)
IR: $\nu$=1683, 1600, 1540, 1330, 745.

EXAMPLE 2

Synthesis of various anilide carboxylic acids

By carrying out the treatment similarly as in Example 1, the captioned compounds shown as compounds Nos. 2 to 31 in Table 1-(1) were obtained.

TABLE 1-(1)

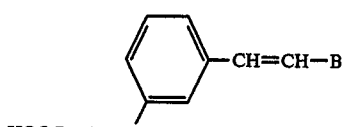

HOOC—A—NH , —CH=CH—B

| Compound No. | A | B | Yield (%) | m.p. (°C.) | IR |
|---|---|---|---|---|---|
| 2 | —CH=CHCO— |  | 87 | 221~224 | 1695, 1550, 1445, 945, 850 |
| 3 | cis 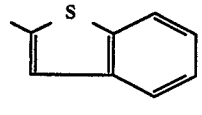 CO— | | 69 | 198~199 | 1720, 1645, 1540, 1180, 740 |
| 4 | —(CH$_2$)$_2$CO— | | 77 | 222~225 | 1710, 1655, 1535, 1245, 940 |
| 5 | —CH=CHCO— | 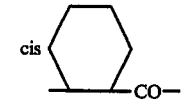 | 98 | 205~206 | 1708, 1610, 1548, 1440, 955, 810 |
| 6 | cis 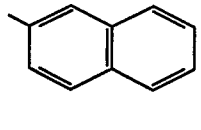 CO— | | 47 | 177~179 | 1705, 1640, 1515, 1183, 740 |
| 7 | —(CH$_2$)$_2$CO— | | 76 | 205~207 | 1695, 1640, 1535, 963, 740 |
| 8 | —CH=CHCO— | —(CH$_2$)$_5$CH$_3$ | 50 | 122~123 | 1700, 1620, 1570, 955, 850 |
| 9 | 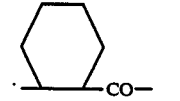 CO— | | 68 | 123~124 | 1715, 1640, 1540, 1180, 955 |
| 10 | (CH$_2$)$_2$CH$_3$<br>\|<br>—CHCH$_2$CO— | 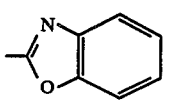 | 96 | 155~156 | 1720, 1655, 1530, 1170, 965 |
| 11 |  CH$_2$CO— | | 94 | 182~184 | 1695, 1660, 1530, 1245, 960 |
| 12 | —C(CH$_3$)$_2$CH$_2$CO— | | 78 | 173~174 | 1690, 1660, 1540, 1425 |
| 13 | CH$_2$CH$_3$<br>\|<br>—CCH$_2$CO—<br>\|<br>CH$_2$CH$_3$ | | 83 | 170~172 | 1690, 1640, 1585, 1550, 1420 |
| 14 | —CH=CHCO— | 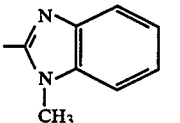 | 83 | 141~143 | 1635, 1545, 1303, 965, 740 |
| 15 | —(CH$_2$)$_2$CO— | | 81 | 208~210 | 1600, 1540, 1490, 960, 740 |

TABLE 1-(1)-continued

HOOC—A—NH— (phenyl) —CH=CH—B

| Compound No. | A | B | Yield (%) | m.p. (°C.) | I R |
|---|---|---|---|---|---|
| 16 | —CH=CHCO— | 2-pyridyl | 90 | 86~89 | 1690, 1635, 1550, 1425, 1300, 780 |
| 17 | —(CH₂)₂CO— | 2-pyridyl | 75 | 167~168 | 1675, 1600, 1545, 1490, 780 |
| 18 | —CH=CHCO— | 6-phenyl-2-pyridyl | 90 | 178~179 | 1725, 1620, 1555, 1435, 840, 745 |
| 19 | —(CH₂)₂CO— | 6-phenyl-2-pyridyl | 84 | 141~143 | 1685, 1655, 1585, 1430, 755 |
| 20 | —CH=CHCO— | 2-quinolyl | 65 | 93~95 | 1678, 1623, 1558, 1420, 750 |
| 21 | —CH=CHCO— | 1-isoquinolyl | 76 | 107~111 | 1710, 1625, 1545, 1380, 770 |
| 22 | —(CH₂)₂CO— | 1-isoquinolyl | 84 | 205~206 | 1688, 1600, 1540, 1490, 740 |
| 23 | —CH=CHCO— | 3-methyl-4-oxo-quinazolin-2-yl | 76 | 197~198 | 1700, 1665, 1540, 850 |
| 24 | —CH=CHCO— | 2-quinazolinyl | 90 | 188~190 | 1708, 1560, 850, 755 |
| 25 | —(CH₂)₂CO— | 2-quinazolinyl | 76 | 213~214 | 1710, 1648, 1583, 1180, 760 |
| 26 | —CH=CHCO— | 2-benzimidazolyl | 95 | 156~158 | 1620, 1545, 1320, 963, 738 |
| 27 | —(CH₂)₂CO— | 2-benzimidazolyl | 87 | 253~254 | 1650, 1540, 1310, 960, 740 |
| 28 | —C(CH₂CH₃)₂CH₂CO— | 2-pyrazinyl | 46 | 136~137 | 1670, 1545, 1030, 960, 860 |
| 29 |  | 2-pyrimidinyl | 85 | 193~194 | 1670, 1580, 1545, 1435, 1180, 1160 |
| 30 |  | 4-methyl-2-pyrimidinyl | 93 | 178~180 | 1680, 1585, 1430, 870, 785 |

TABLE 1-(1)-continued

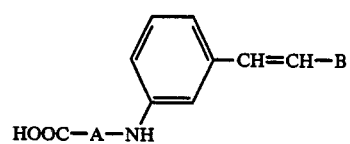

| Compound No. | A | B | Yield (%) | m.p. (°C.) | IR |
|---|---|---|---|---|---|
| 31 | | 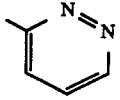 | 74 | 177~179 | 1685, 1585, 1550, 1425, 1200, 960 |

EXAMPLE 3

Synthesis of 2-[trans-3-(3-carboxypropanamide)styryl]quinoline.-sodium salt (compound No. 32)

To 10 ml of methanol were added 100 mg of 2-[trans 3-(3-carboxypropanamide)styryl]quinoline and 1 ml of an aqueous solution containing 24 mg of sodium hydrogencarbonate, and the mixture was heated for 2 hours under reflux. After cooled to room temperature, the filtrate obtained by filtration was concentrated, followed by drying under reduced pressure to give 104 mg (yield: 98%) of the captioned compound.

m.p.: 203°–211° C.,
IR: $\nu$ = 1560, 1420, 815, 740.

EXAMPLE 4

Synthesis of sodium salts of carboxylic acid having various styryl group

By carrying out the treatment similarly as in Example 3, the captioned compounds shown as compounds Nos. 33 to 45 in Table 1-(2) were obtained.

TABLE 1-(2)

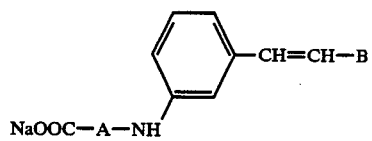

| Compound No. | A | B | Yield (%) | m.p. (°C.) | IR |
|---|---|---|---|---|---|
| 33 | —CH=CHCO— |  | 82 | 265~268 | 1660, 1555, 1430, 940, 740 |
| 34 | 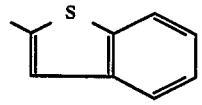 cis —CO— | | 87 | >290 | 1670, 1560, 1410, 940, 740 |
| 35 | —(CH$_2$)$_2$CO— | | 93 | 270~274 | 1658, 1640, 1550, 1420, 940, 670 |
| 36 | —CH=CHCO— |  | 100 | 278~280 | 1655, 1565, 1440, 955 |
| 37 | 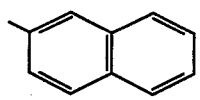 cis —CO— | | 89 | 271~273 | 1680, 1600, 1530, 1400, 960, 740 |
| 38 | —(CH$_2$)$_2$CO— | | 88 | 262~264 | 1650, 1560, 1410, 960, 740 |
| 39 | —CH=CHCO— | —(CH$_2$)$_5$CH$_3$ | 64 | 133~136 | 1660, 1560, 1435, 1350, 960 |
| 40 |  —CO— | | 90 | 181~185 | 1660, 1600, 1560, 1410, 960 |
| 41 | —C(CH$_3$)$_2$CH$_2$CO— | 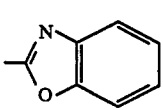 | 100 | 160~161 | 1635, 1545, 1410, 1240 |
| 42 | CH$_2$CH$_3$ \| —CCH$_2$CO— \| CH$_2$CH$_3$ | | 100 | 165~167 | 1640, 1545, 1450, 1245, 970 |

TABLE 1-(2)-continued

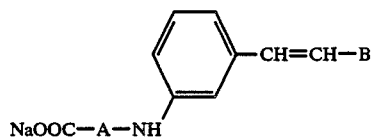

| Compound No. | A | B | Yield (%) | m.p. (°C.) | IR |
| --- | --- | --- | --- | --- | --- |
| 43 | —CH=CHCO— | ![benzimidazole with N-CH3] | 17 | deliquescent | 1665, 1560, 1440, 740 |
| 44 | —(CH₂)₂CO— | ![benzimidazole with N-CH3] | 15 | deliquescent | 1665, 1555, 1400, 740 |
| 45 | —CH=CHCO— | ![quinoline] | 83 | 151~162 | 1555, 1420, 1310, 745 |

EXAMPLE 5

Synthesis of 2-[trans-3-(3-carboxypropylamino)styryl]-1-methylbenzimidazole (compound No. 46)

To 10 ml of toluene were added 1.0 g of 2-(trans-3-aminostyryl)-1-methylbenzimidzole and 784 mg of ethyl 4-bromobutylate, and the mixture was heated for 5 hours under reflux. After cooled to room temperature, the reaction mixture was extracted with ethyl acetate in an ordinary manner. The residue from the extract was purified through silica gel column chromatography to give 426 mg of the ethyl ester as an oily substance. This oily substance was dissolved in 10 ml of ethanol and was added thereto 0.8 ml of aqueous solution containing 165 mg of sodium hydroxide. The reaction was carried out at 60° C. for 3 hours to effect hydrolysis. After completion of the reaction, ethanol was distilled off and to the residue was added 1 ml of water and 3 ml of 5% hydrochloric acid solution under ice-cooling. The precipitates formed were collected by filtration, followed by drying under reduced pressure to give 279 mg of the free caboxylic acid. Further, this acid was dissolved in 5 ml of methanol and was added thereto 1 ml of aqueous solution containing 145 mg of sodium hydrogencarbonate, followed by stirring at 60° C. for 2 hours. The solvent was distilled off and to the residue was added 10 ml of ethanol. After removal of the insoluble substance by filtration, to the filtrate was added ethyl ether, and the precipitates formed were collected by filtration, followed by drying to give 276 mg (total yield: 27%) of the captioned compound.

m.p.: 90°–95° C. (decomposition),
IR: $\nu$=1600, 1560, 1400, 740.

EXAMPLE 6

Preparation of tablets

An amount of 1000 g of well pulverized 2-[trans-3-(3-carboxypropanamide)styryl]quinoline.sodium salt (compound No. 32), 5900 g of lactose, 2000 g crystalline cellulose, 1000 g of a low substitution degree hydroxypropyl cellulose and 100 g of magnesium stearate were well mixed and formed according to the direct tableting method into plain tablets containing 10 mg of the above compound in 100 mg of one tablet. The plain tablet was applied with sugar coating or film coating to prepare sugar-coated tablet and film-coated tablet.

EXAMPLE 7

Preparation of capsules

An amount of 1000 g of well pulverized 2-[trans-3-(3-carboxypropanamide)styryl]quinoline.sodium salt (compound No. 32), 3000 g of corn starch, 6900 g of lactose, 1000 g of crystalline cellulose and 100 g of magnesium stearate were mixed to prepare capsules containing 10 mg of the above compound in 120 mg of one capsule.

EXAMPLE 8

Preparation of inhalent

An amount of 5 g of well pulverized 2-[trans-3-(3-carboxypropanamide)styryl]quinoline.sodium salt (compound No. 32), 10 g of a middle chain saturated fatty acid triglyceride and 0.2 g of sorbitane monooleate were well mixed, and each 15.2 mg of the mixture was weighed in 5 ml of an aluminum vessel for aerosol. Further, after 84.8 mg of Freon 12/114 (1:1 mixture) was filled per one vessel at low temperature, the vessel was equipped with a quantitative adaptor of 100 μl per 1 spray to prepare an inhalent of quantitative spray containing 5 mg of the above compound in one vessel having a capacity of 5 ml.

EXAMPLE 9

SRS antagonistic action in vitro

The ileum end portion of a male Hartley-strain guinea pig weighing 200–450 g was extirpated and after washing its lumen, the ileum was mounted within tissue bath containing 5 ml of a Tylord solution comprising the following components. The components are 136 mM NaCl, 2.7 mM KCl, 11.9 mM NaHCO₃, 1.05 mM MgCl₂, 1.8 mM CaCl₂, 0.4 mM NaH₂PO₄ and 5.6 mM glucose. The liquid temperature in the bath was maintained at 37° C., and aeration was effected with 95% oxygen/5% carbon dioxide. For removing shrinkage with hystamine and acetylcholine, $10^{-7}$ g/ml of mepylamin and $5\times10^{-8}$ g/ml of atropin were added to the above buffer. Isotonic measurement was conducted by isotonic transducer (TD-112S, trade name, produced by Nippon Koden) tension replacement convertor and recorded by Recticoder (RTG-4124, trade name, produced by Nippon Koden) as the change in grams of tension. The ileum was loaded passively with 0.5 g of tension and the ileum shrinkage reaction to SRS extracted from guinea pig lung was obtained. The persistent shrinkage height by one unit of of SRS (corresponding to 5 ng of hystamine) was used as control.

Test drugs of various concentrations were added into the tissue bath, and the results of minimum effective concentration which is the concentration of the test drug attenuating shrinkage of control to 50% ($IC_{50}$) are shown in Table 2.

TABLE 2

| Compound No. | Minimum effective concentration |
|---|---|
| 1 | $2 \times 10^{-8}$ |
| 14 | $10^{-7}$ |
| 15 | $5 \times 10^{-7}$ |
| 16 | $10^{-5}$ |
| 19 | $10^{-5}$ |
| 20 | $5 \times 10^{-9}$ |
| 23 | $10^{-5}$ |
| 24 | $5 \times 10^{-7}$ |
| 25 | $10^{-5}$ |
| 26 | $10^{-5}$ |
| 32 | $2 \times 10^{-8}$ |
| 34 | $10^{-5}$ |
| 39 | $10^{-5}$ |
| 40 | $10^{-5}$ |
| 43 | $10^{-7}$ |
| 44 | $5 \times 10^{-7}$ |
| 45 | $5 \times 10^{-8}$ |
| 46 | $5 \times 10^{-8}$ |

TEST EXAMPLE

Acute toxicity test

With 4 to 5 ddy-strain male mice of 6 weeks old as one group, the compound of the present invention was orally administered as a suspension in 1% tragacanth solution, and observation was conducted for 7 days and the number of dead mice was examined to obtain the results shown in Table 3.

TABLE 3

| Compound No. | Value of acute toxicity ($LD_{50}$ mg/kg) |
|---|---|
| 32 | >1000 |
| 45 | >1000 |

We claim:

1. An aminostyryl compound represented by Formula I:

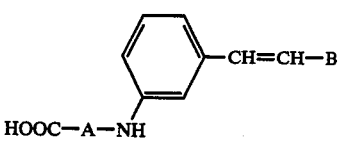

(I)

wherein A represents a linking group having 3 to 4 chain members; B represents an unsubstituted or substituted 5 to 6-membered monocyclic type heterocyclic residue containing 1 to 2N hetero atoms, an unsubstituted or substituted condensed heterocyclic residue which contains 5 to 6-membered monocyclic type heterocyclic containing 1 to 2N hetero atoms, or a pharmaceutically acceptable salt thereof.

2. The aminostyryl compound according to claim 1, wherein said linking group having 3 to 4 chain members for A is —CH=CHCO—, —(CH₂)ₘCO— (wherein m represents an integer of 2 to 3), —(CH₂)ₙ— (wherein n represents an integer of 3 to 4),

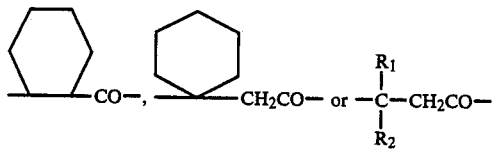

(wherein $R_1$ and $R_2$ each independently represent a hydrogen atom or an alkyl group having 1 to 4 carbon atoms);

said unsubstituted or substituted 5 to 6-membered monocyclic type heterocyclic residue containing 1 to 2 hetero atoms for B is pyrrolyl, pyrrolinyl, pyrrolidinyl, imidazolyl, imidazolinyl, imidazolidinyl, pyrazolyl, pyrazolinyl, pyrazolidinyl pyridyl, pyrimidinyl, pyrazinyl, pyranyl, piperidyl, pyridazinyl or piperazinyl and said condensed heterocyclic residue for B is one in which monocyclic type heterocycle as described above for the monocyclic type heterocyclic residue and a benzene ring are condensed.

3. The aminostyryl compound according to claim 1, wherein A is

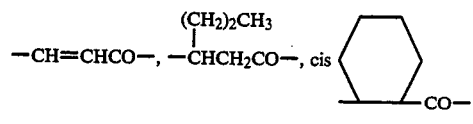

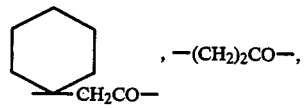

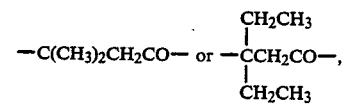

B is

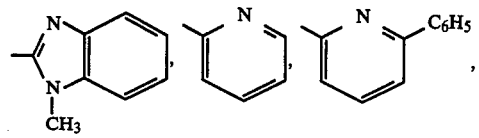

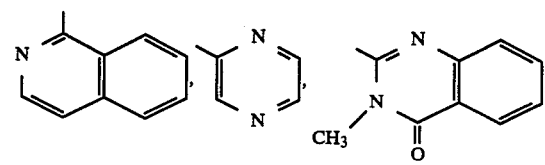

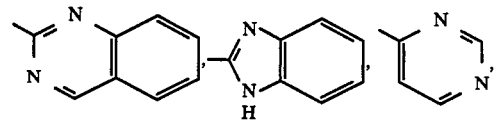

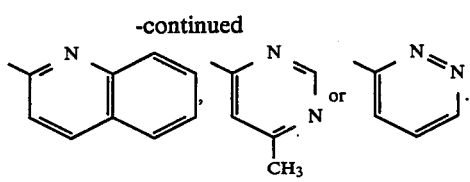

4. The aminostyryl compound according to claim 1, wherein said compound is selected from the group consisting of 2-[trans-3-(3-carboxypropanamide)styryl]-quinoline, 2-[trans-3-(3-carboxypropenamide)styryl]-quinoline, 2-[trans-3-(3-carboxypropylamine)styryl]-1-methylbenzimidazole and 2-[trans-3-(3-carboxypropanamide)styryl]quinoline sodium salt.

5. A composition having leukotriene antagonism which comprises an aminostyryl compound represented by Formula I:

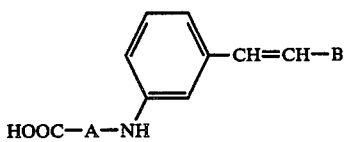

(I)

wherein A represents a linking group having 3 to 4 chain members; B represents an unsubstituted or substituted 5 to 6-membered monocyclic type heterocyclic residue containing 1 to 2 N-hetero atoms, an unsubstituted or substituted condensed heterocyclic residue which contains 5 to 6-membered monocyclic type heterocycle containing 1 to 2 N-hetero atoms, or a pharmaceutically acceptable salt thereof, and a pharmaceutically acceptable carrier.

6. The composition according to claim 5, wherein said linking group having 3 to 4 chain members for A is —CH=CHCO—, —(CH$_2$)$_m$CO— (wherein m represents an integer of 2 to 3), —(CH$_2$)$_n$— (wherein n represents an integer of 3 to 4),

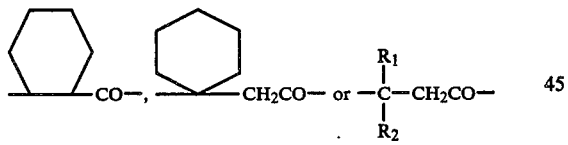

(wherein R$_1$ and R$_2$ each independently represent a hydrogen atom or an alkyl group having 1 to 4 carbon atoms);

said unsubstituted or substituted 5 to 6-membered monocyclic type heterocyclic residue containing 1 to 2 N-hetero atoms for B is pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, pyrazinyl, pyranyl, piperidyl, pyridazinyl or piperazinyl; and said condensed heterocyclic residue for B is one in which monocyclic type heterocycle as described above for the monocyclic type heterocyclic residue and a benzene ring are condensed.

7. The composition according to claim 5, wherein A is

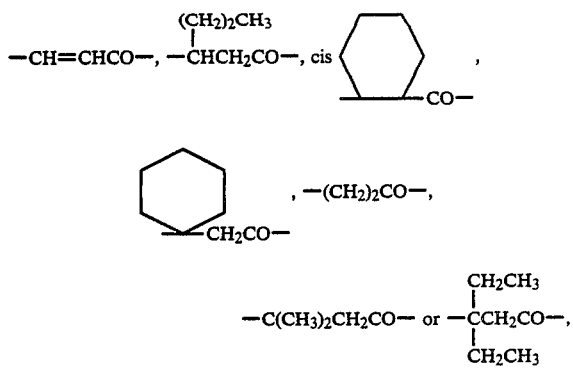

B is

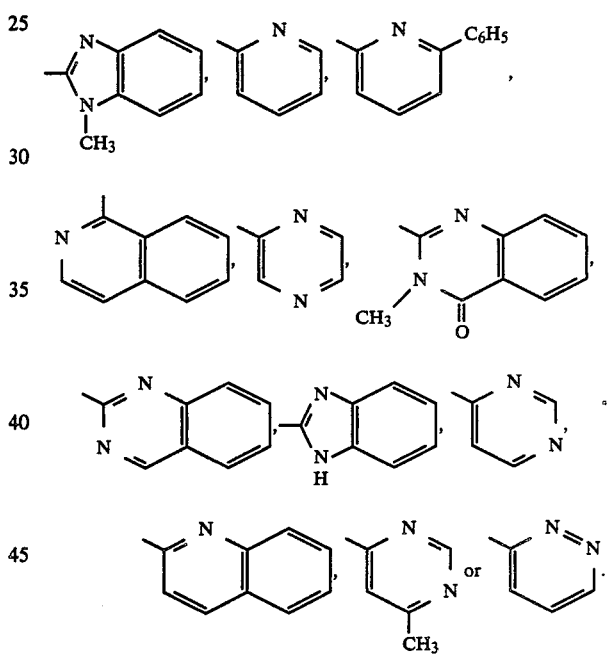

8. The composition according to claim 5, wherein said compound is selected from the group consisting of 2-[trans-3-(3-carboxypropanamide)styryl]quinoline, 2-[trans-3-(3-carboxypropenamide)styryl]quinoline, 2-[trans-3-(3-carboxypropylamine)styryl]-1-methylbenzimidazole and 2-[trans-3-(3-carboxypropanamide)-styryl]quinoline sodium salt.

* * * * *